United States Patent [19]

Harandi et al.

[11] Patent Number: 5,313,004
[45] Date of Patent: May 17, 1994

[54] PRODUCTION OF ALKYL TERTIARY ALKYL, ETHERS FROM ISOALKANES

[75] Inventors: Mohsen N. Harandi, Langhorne, Pa.; Paul J. Oswald, Voorhees, N.J.

[73] Assignee: Mobil Oil Corporation, Fairfax, Va.

[21] Appl. No.: 7,317

[22] Filed: Jan. 21, 1993

Related U.S. Application Data

[63] Continuation-in-part of Ser. No. 726,418, Jul. 5, 1991, abandoned.

[51] Int. Cl.$^5$ .................. C07C 41/00; C07C 43/00
[52] U.S. Cl. ........................................... 568/697
[58] Field of Search ................................. 568/697

[56] References Cited

U.S. PATENT DOCUMENTS 4,826,507  5/1989  Haranda et al. ............... 568/697
4,906,788  3/1990  Scott et al. .................... 568/697

OTHER PUBLICATIONS

Perry et al., Chemical Engineers Handbook, McGraw Hill, 1973, pp. 17-34 to 17-37.

Primary Examiner—Marianne M. Cintins
Assistant Examiner—Rebecca Cook
Attorney, Agent, or Firm—Alexander J. McKillop; Malcolm D. Keen; Wise L. Gene

[57] ABSTRACT

A process is disclosed for integrating isoalkane dehydrogenation with isoalkene/alkanol etherification in a manner that eliminates the need to condense the isoalkene and/or isoalkane components of the dehydrogenation process in order to produce alkyl tertiary alkyl ethers. The novel process integration permits recycling of unreacted isoalkene and/or isoalkane components of the integrated dehydrogenation and etherification process back to the dehydrogenation reactor with revaporization. It has been determined that isoalkane dehydrogenation can be integrated with vapor phase etherification by pressuring the dehydrogenation effluent and passing compressed isoalkene to the vapor phase etherification zone. Following etherification and separation of the etherification effluent, unreacted isoalkene and isoalkane vapor components of the etherification effluent are recycled to the dehydrogenation zone. Optionally, unreacted isoalkene is oligomerized in contact with medium pore shape selective zeolite catalyst.

5 Claims, 2 Drawing Sheets

PRODUCTION OF ALKYL TERTIARY ALKYL, ETHERS FROM ISOALKANES

REFERENCE TO COPENDING APPLICATION

This application is a continuation-in-part of U.S. patent application Ser. No. 07/726,418 filed 5 July 1991, now abandoned incorporated herein by reference.

FIELD OF INVENTION

This invention relates to a process for the production of alkyl tertiary alkyl ethers from isoalkanes or isoparaffins. The invention particularly relates to an integrated process for dehydrogenation of isoalkanes to isoalkenes followed etherification with lower alkanol to produce high octane value tertiary alkyl ethers, such as methyl t-butyl ether (MTBE) or t-amyl methyl ether (TAME).

BACKGROUND OF THE INVENTION

It is known that isobutene and other isoalkenes (tertiary olefins) produced by hydrocarbon cracking may be reacted with methanol or other $C_1$-$C_3$ lower aliphatic alcohols over an acidic catalyst to provide tertiary butyl ether, especially MTBE and TAME. Generally, it is known that asymmetrical ethers having the formula $(CH_3)_3C$-O-R, where R is a $C_1$-$C_4$ alkyl radical, are particularly useful as octane improvers for liquid fuels, especially gasoline.

MTBE, ethyl t-butyl ether (ETBE), TAME and isopropyl t-butyl ether (IPTBE) are known to be high octane ethers. The article by J.D. Chase, et al., *Oil and Gas Journal*, April 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Liquid phase reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo," by J.D. Chase, et al., *The Oil and Gas Journal*, April 9, 1979, pages 149-152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable. Typically, with acid resin catalyst the etherification reaction is carried out in liquid phase. However, vapor phase and mixed phase etherification is known, particularly where the catalyst is contained as a fixed bed in a catstill type fractionator which serves to both separate the reaction products and operate as a vessel to contain the catalyst under etherification conditions.

Typical hydrocarbon feedstock materials for etherification reactions include olefinic streams, such as cracking process light gas containing butene isomers in mixture with substantial amounts of paraffins including n-butane and isobutane. The $C_4$ components usually contain a major amount of unsaturated compounds, such as 10-40% isobutene, 20-55% linear butenes, and small amounts of butadiene. Also, $C_4+$ heavier olefinic hydrocarbon streams may be used, particularly mixtures of isobutene and isoamylene and $C_5+$ streams containing isoamylene.

Isoalkanes such as isobutane and isopentanes can be dehydrogenated to isoalkenes or tertiary olefins such as isobutene and isoamylenes and etherified with methanol to provide MTBE and TAME.

Dehydrogenation of isoalkanes in the vapor phase is well known in the art to produce isoalkenes. When in the prior art dehydrogenation is integrated with etherification to produce MTBE and TAME, isoalkene vapor from dehydrogenation is first condensed to employ as a feedstream in the conventional liquid phase etherification of iso-olefins of tertiary alkyl ethers. Following etherification, unconverted iso-olefins is the etherification reactor effluent are vaporized to recycle them to the dehydrogenation reactor. Prior integrated dehydrogenation-etherification process require at least two phase changes with significant energy losses and inefficiencies associated with these changes as well as the need for multiple heat exchangers.

U.S. Pat. No. 4,605,787 to Chu et al., incorporated herein by reference, describes a process for the preparation of methyl tertiary butyl ether which comprises reacting isobutene and methanol in the vapor phase in the presence of zeolite catalyst. Under the conditions described for the vapor phase etherification, side reactions, particularly the dimerization of isobutene, are virtually eliminated. The reaction products are essentially MTBE and unreacted methanol and/or isobutene.

U.S. Pat. No. 5,008,467 to Vora et al. describes a process for direct etherification of a dehydrogenation effluent using liquid phase etherification. Light components are not purged in a membrane system; nor is a single tower used to debutanize the MTBE product and recover MTBE product. Conventional practices are followed as well with respect to the provision of a reflux stream for the fractionator employed in the process of Vora et al.

It is an object of the present invention to provide an improved process for the production of alkyl tertiary butyl ether or alkyl tertiary amyl ether from isobutane and/or isopentane.

A further object of the invention is to provide a substantially vapor phase integrated process for dehydrogenation of isoalkanes and etherification of resultant isoalkenes to tertiary alkyl ethers.

Another object of the invention is to improve the overall energy efficiency of converting isoalkanes to alkyl tertiary alkyl ethers by avoiding the need to condense at least a major portion of the effluent from dehydrogenation of isoalkane and revaporize the effluent from isoalkene etherification so that unreacted isoalkene or isoalkane can be recycled to the dehydrogenation vessel.

SUMMARY OF THE INVENTION

A process has been discovered for integrating isoalkane dehydrogenation with isoalkene/alkanol etherification in a manner that eliminates the need to condense at least a major portion of the isoalkene and/or isoalkane components of the dehydrogenation process in order to produce alkyl tertiary alkyl ethers. The novel process integration permits recycling of unreacted isoalkene and/or isoalkane components of the integrated dehydrogenation and etherification process back to the dehydrogenation reactor with preferably no phase change. It has been determined that isoalkane dehydrogenation can be integrated with etherification by pressuring the dehydrogenation effluent and passing compressed isoalkene to the vapor phase or mixed vapor-liquid phase etherification zone. Following etherification and separation of the etherification effluent, unreacted isoalkene and isoalkane vapor components of the etherification effluent are recycled to the dehydrogenation zone.

More particularly, a process for the production of alkyl tertiary alkyl ethers has been discovered comprising contacting a hydrocarbon feedstream rich in iso-olefins and a $C_1-C_3$ alkanol feedstream with acidic etherification catalyst in an etherification zone under vapor phase etherification conditions whereby an effluent stream is produced comprising alkyl tertiary alkyl ethers, unreacted $C_1-C_3$ alkanol, and hydrocarbons. Advantageously, the effluent stream may be passed to a fractionator and separated in contact with a reflux stream comprising fresh hydrocarbon feedstock rich in isoparaffins whereby a bottom liquid stream is recovered comprising said ethers and an overhead vapor stream is separated comprising said unreacted alkanol and hydrocarbons rich in isoparaffins. The overhead vapor stream is introduced to a dehydrogenation zone in contact with dehydrogenation catalyst under dehydrogenation conditions whereby a dehydrogenation effluent vapor stream is produced rich in tertiary olefin and hydrogen. The dehydrogenation effluent is compressed and hydrogen separated therefrom. The residue from said compressed dehydrogenation effluent after hydrogen separation comprises said hydrocarbon feedstream rich in olefin which is passed to said etherification zone.

The utilization of fresh hydrocarbon feedstream rich in isoparaffins as a reflux stream to the fractionator is a surprisingly efficacious advantage of the instant invention. Optionally, the fresh feedstream can be expanded through appropriate valving to lower the temperature of the feedstream as fed to the fractionator. This reduces the overall operating pressure requirements of the fractionator which can operate without a conventional overhead condensing system.

The invention also includes a process for the production of high octane number alkyl tertiary alkyl ethers from isoparaffins, comprising:

a) introducing a hydrocarbon feedstream rich in isoparaffin into a dehydrogenation zone containing dehydrogenation catalyst under dehydrogenation conditions whereby a vaporous effluent stream is produced comprising tertiary olefin and hydrogen;

b) compressing and separating said effluent stream to recover a stream comprising said iso-olefins at elevated pressure and a by-product stream comprising said hydrogen, wherein said separation step comprises vapor phase separation employing a membrane as separator means;

c) contacting step (b) t-olefin stream and $C_1-C_3$ alkanol feedstream with acidic etherification catalyst under predominantly vapor phase (at least 50-80 wt % vapor) etherification conditions in an etherification zone whereby an etherification zone effluent stream is produced comprising said alkyl tertiary alkyl ethers, unreacted alkanol and unreacted iso-olefins; and d) separating said etherification zone effluent stream to recover said alkyl tertiary alkyl ethers.

In another embodiment of the instant invention vapor phase etherification of tertiary-olefin is carried out on the effluent from dehydrogenation upstream of the compressor. For instance, compressed dehydrogenation effluent is etherified, and etherification effluent is separated into a light gas ($H_2$) stream, isobutane-rich recycle stream, and an ether-rich stream by distillation followed by membrane separation of compressed distillation overhead gas. In this configuration, MTBE can be produced which can be separated before compression to minimize the quantity of material being fed to the compressor. Following compression, light gases can be removed by membrane separation and a second etherification step carried out in vapor phase or mixed vapor-liquid phase, preferably employing a fractionator containing a fixed bed of acidic catalyst.

DETAILED DESCRIPTION OF THE INVENTION

Figure 1:
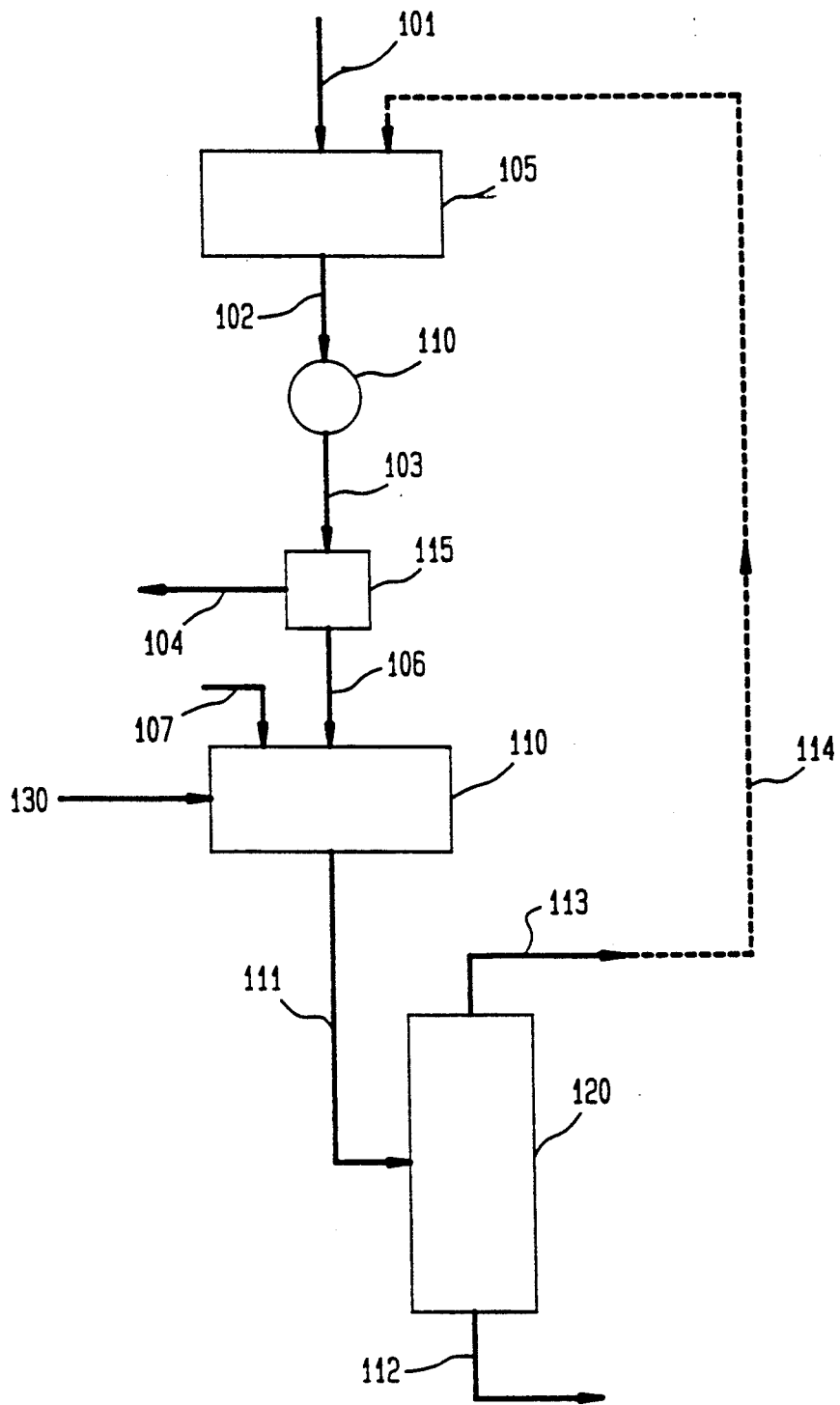
FIG. 1 is a schematic diagram of the process of the invention containing the major elements of dehydrogenation, etherification and separation of the etherification effluent.

The invention comprises an integrated design for dehydrogenation and etherification to produce MTBE and TAME more efficiently from isobutane and isopentane. In the preferred mode the dehydrogenation reactor effluent is pressurized and sent as a vapor, substantially free of liquid phase, to an etherification zone. The ether product is fractionated in a debutanizer or the like, which preferably uses the hydrocarbon feed as the reflux to the fractionation tower. The fractionator overhead provides combined feed to the dehydration zone. The hydrogen byproduct from dehydrogenation is preferably separated from the dehydrogenation reactor effluent upstream of the etherification zone in a membrane separation system.

The novel design advantageously maintains the entire dehydrogenation recycle loop in the vapor phase. As a result, the need to condense the dehydrogenation reactor effluent and vaporize the unconverted etherification reactor effluent to provide recycle stream to the dehydrogenation zone is eliminated. In addition, if hydrogen recycle is employed, it may be recycled to the dehydrogenation zone without separating it from the unconverted butanes. The opportunity provided in the present invention to recycle hydrogen containing light gases such as unconverted butanes without further separation represents a significant economic advantage. In a preferred embodiment, net hydrogen produced in the process is removed from the system by membrane separation. Hydrogen can be selectively recovered via membrane from dehydrogenation effluent or at least a portion of etherification effluent, for instance, by compressing an isobutane-rich stream containing hydrogen. The membrane separation step can also function to purge $C_1-C_3$ byproduct with the hydrogen-rich offgas.

In one embodiment of the invention, the unconverted etherification reaction effluent is preferably sent to the dehydrogenation zone where it is upgraded to hydrocarbons. Optionally, the olefin and alkanol in the dehydrogenation reactor feed can be upgraded in a catalytic olefin to gasoline ("MOG") reactor zone under known conditions for the conversion of methanol and/or olefins to gasoline. Such reaction zone may be a small bed of ZSM-5 catalyst disposed adjacent to the dehydrogenation catalyst bed. Optionally, the olefinic gasoline may be aromatized in the dehydrogenation zone and the aromatics can be separated from the dehydrogenation reactor effluent in the etherification fractionator. The optional conversion step can convert the methanol, diolefins and olefins in the MTBE debutanizer overhead which allows high excess methanol to be used in the etherification step. Incorporating an olefins upgrading process step avoids using hydrogen saturation units for removing olefins and essentially eliminates the need for a methanol recovery section downstream of the debutanizer.

The olefins upgrading ("MOG") process preferred in the present invention is well-known in the petroleum refining arts and provides a system for upgrading light olefins to liquid hydrocarbons, utilizing a continuous process for producing fuel products by oligomerizing olefinic components to produce higher hydrocarbon products for use as fuel or the like. The preferred MOG feedstock contains $C_2$-$C_4$ alkenes (mono-olefin) in the range of about 10 to 90 wt %. Non-deleterious components, such as methane and other paraffins and inert gases, may be present. The process may be tolerant of a wide range of lower alkanes, from 0 to 90%.

Conversion of lower olefins, especially ethene, propene and butenes, over HZSM-5 is effective at moderately elevated temperatures and pressures. Operating details for typical olefin oligomerization units are disclosed in U.S. Pat. Nos. 4,456,779; 4,497,968 (Owen et al.) and 4,433,185 (Tabak), incorporated herein by reference. The conversion of paraffins and/or olefins to aromatics, i.e. M-2 Forming, is described in U.S. Pat. Nos. 3,760,024 and 3,756,942 to Cattanach, U.S. Pat. No. 3,845,150 to Yan et al., U.S. Pat. No. 4,090,949 to Owen et al. These patents are also incorporated herein by reference in their entirety.

Catalysts useful in the MOG process and the process of the instant invention include a unique group of metallosilicate zeolites. Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion and the process of the present invention includes the medium pore (i.e., about 5-7 angstroms) shape selective crystalline aluminosilicate zeolites having a silica to alumina ratio of about 20:1 or greater, a constraint index of about 1-12, and acid cracking activity (alpha value) of about 2-200. Representative of the shape selective zeolites are ZSM-5, ZSM-11, ZSM-12, ZSM-22, ZSM-23, ZSM-35 and ZSM-48. ZSM-5 is disclosed in U.S. Pat. No. 3,702,886 and U.S. Pat. No. Reissue 29,948. Other suitable zeolites disclosed in U.S. Patent Nos. 3,709,979 (ZSM-11); 3,832,449 (ZSM-12); 4,076979; 4,076842 (ZSM-23); 4,016,245 (ZSM-35 ); and 4,375,573 (ZSM-48). The disclosures of these patents are incorporated herein by reference.

The present integrated invention incorporates dehydrogenation of fresh or recycled unreacted $C_4$-$C_5$ isoparaffins to iso-olefins to provide a hydrocarbon feedstream rich in $C_4$-$C_5$ iso-olefins comprising isobutene and isoamylene for etherification. It is known that the conversion of paraffins to monoolefins such as isobutene and isoamylene can be accomplished by thermal or catalytic dehydrogenation. A general discussion of thermal dehydrogenation (i.e., steam cracking) is presented in *Encyclopedia of Chemical Technology*, Ed. by Kirk and Othmer, Vol. 19, 1982, Third Ed., pp. 232-235. Various processes for catalytic dehydrogenation are available in the prior art. These processes include the Houdry Catofin process of Air Products and Chemical, Inc., Allentown, Pa., the Oleflex process of UOP, Inc., Des Plaines, Ill. and a process disclosed by U.S. Pat. No. 4,191,846 to Farha, Jr. et al. The Houdry Catofin process, described in a magazine article, "Dehydrogenation Links LPG to More Octanes", Gussow et al, *Oil and Gas Journal*, Dec. 8, 1980, involves a fixed bed, multi-reactor catalytic process for conversion of paraffins to olefins. Typically, the process runs at low pressures of 5-30 inches of mercury absolute, and high temperatures with hot reactor effluent at 550°-650° C. Dehydrogenation is an endothermic reaction, so it normally requires a furnace to provide heat to a feed stream prior to feeding the feed stream into the reactors. The UOP Oleflex process, disclosed in an article "$C_2/C_5$ Dehydrogenation Updated", Verrow et al, *Hydrocarbon Processing*, April 1982, used stacked catalytic reactors. U.S. Pat. No. 4,191,846 to Farha, Jr. et al teaches the use of group VIII metal containing catalysts to promote catalytic dehydrogenation of paraffins to olefins. It is also known that shape selective medium pore zeolite such as ZSM-5 can be prepared containing active dehydrogenation catalyst. Representative examples include ZSM-5 containing platinum and tin, thalium, iridium, lead and/or indium. Suitable materials are disclosed by Dessau et al. in U.S. Pat. Nos. 4,849,567; 4,922,050 and 4,931,416.

As disclosed in the previously cited U.S. Pat. No. 4,605,787 to Chu et al, etherification of isobutene with methanol can be carried out in the vapor phase at temperatures between 77° C. and 105° C. in contact with acidic ZSM-5, ZSM-11, ZSM-12 or MCM-22 to produce MTBE in high conversion and selectivity. The process is distinguished by the fact that the formation of isobutene dimer byproduct is virtually eliminated. It is also known that etherification to produce MTBE can be carried out in a mixed vapor-liquid phase in contact with acidic resin catalyst.

In the etherification process it is known that alkanol and tertiary iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalency basis, equimolar quantities of alkanol and iso-olefins are advantageous but an excess between 2 and 200% of either component can be passed to the etherification reaction unit. In the present invention, the molar ratio of alkanol to iso-olefin, such as methanol to isobutylene, can be between 0.7 and 2, but preferably the molar ratio is 1 for methanol to isobutene in liquid phase etherification. Advantageously, the excess methanol may be about 40% or more when the hydrocarbon feedstream comprises significant quantity of isoamylenes, but equimolar quantities are preferred when the hydrocarbon feedstream iso-olefin component consists essentially of $C_4$ hydrocarbons. In the instant invention, since a high recycle ratio is used and the feed is used as reflux to the fractionator, relatively high excess methanol can be used since the diluents present allow higher methanol flow rate in the azeotropic mixture that can be formed in the tower.

Iso-olefins or isoalkenes in this invention are those having the formula $R_2C=CH_2$ or $R_2C=CHR$, particularly $C_4$–$C_7$ iso-olefins. Alkanols which may be used in the present invention include methanol, ethanol, 1-propanol, isopropanol, 1-butanol and 2-butanol. The term lower alkyl refers to $C_1$–$C_4$ alkyl including methyl, ethyl, n-propyl and/or isopropyl. For purposes of explanation, MTBE production from $C_4$ hydrocarbons is described in detail herein.

Referring to FIG. 1, a simplified process flow diagram for a preferred embodiment of the invention is presented for the vapor phase etherification of isobutene with methanol to produce methyl tert-butyl ether wherein the isobutene feedstream to etherification is produced by dehydrogenation of isobutane.

In this embodiment, a hydrocarbon feedstream 101 that is rich in isobutane is passed to a dehydrogenation reactor 105. In the dehydrogenation reactor preferably employing catalytic dehydrogenation conditions and catalysts well known in the art, isobutane is converted to isobutene and hydrogen. The dehydrogenation reactor effluent 102 is pressurized in compressor 110 and passed 103 to a vapor phase separator such as a membrane separator 115. Membrane separation of the pressurized dehydrogenation reactor effluent is carried out employing processes and conditions well known in the art for separation of hydrogen in a mixture of gases comprising light hydrocarbons and hydrogen, such as cellulose acetate, polyamide, polyimides or other selectively porous membranes. Suitable membrane separation units, such as "Prism" separators, are described in U.S. Pat. No. 5,082,481 (Barchas et al).

Following membrane separation the hydrogen component of the dehydrogenation effluent stream 104 is purged. The hydrocarbon rich fraction from the membrane separation process comprising isobutene at elevated pressure along with a alkanol feedstream 107, preferably methanol and an optional iso-olefin rich stream 130, is introduced to a vapor phase etherification zone 110 for vapor phase etherification of isobutene to MTBE under conditions known in the art and as carried out in the previously cited reference to Chu. From the vapor phase etherification zone an effluent stream 111 is passed to a debutanizer or depentanizer/debutanizer 120. The composition of the effluent stream includes MTBE, unreacted methanol plus unreacted isobutene and other olefins and paraffins either initially contained in feedstream 101 or olefins produced in dehydrogenation zone 105. Separation is carried out in the debutanizer to produce a bottom stream 112 comprising MTBE and/or TAME and an overhead stream 113 containing unreacted alkanol, $C_4$- and/or $C_5$- olefins and paraffins. Unreacted alkanol in stream 113 as well as unreacted olefins can be separated by extraction and/or distillation techniques well known in the prior art. As illustrated in FIG. 1 by dash line 114, the overhead stream containing unconverted olefins and paraffins can be recycled to dehydrogenation zone 105.

Figure 2:
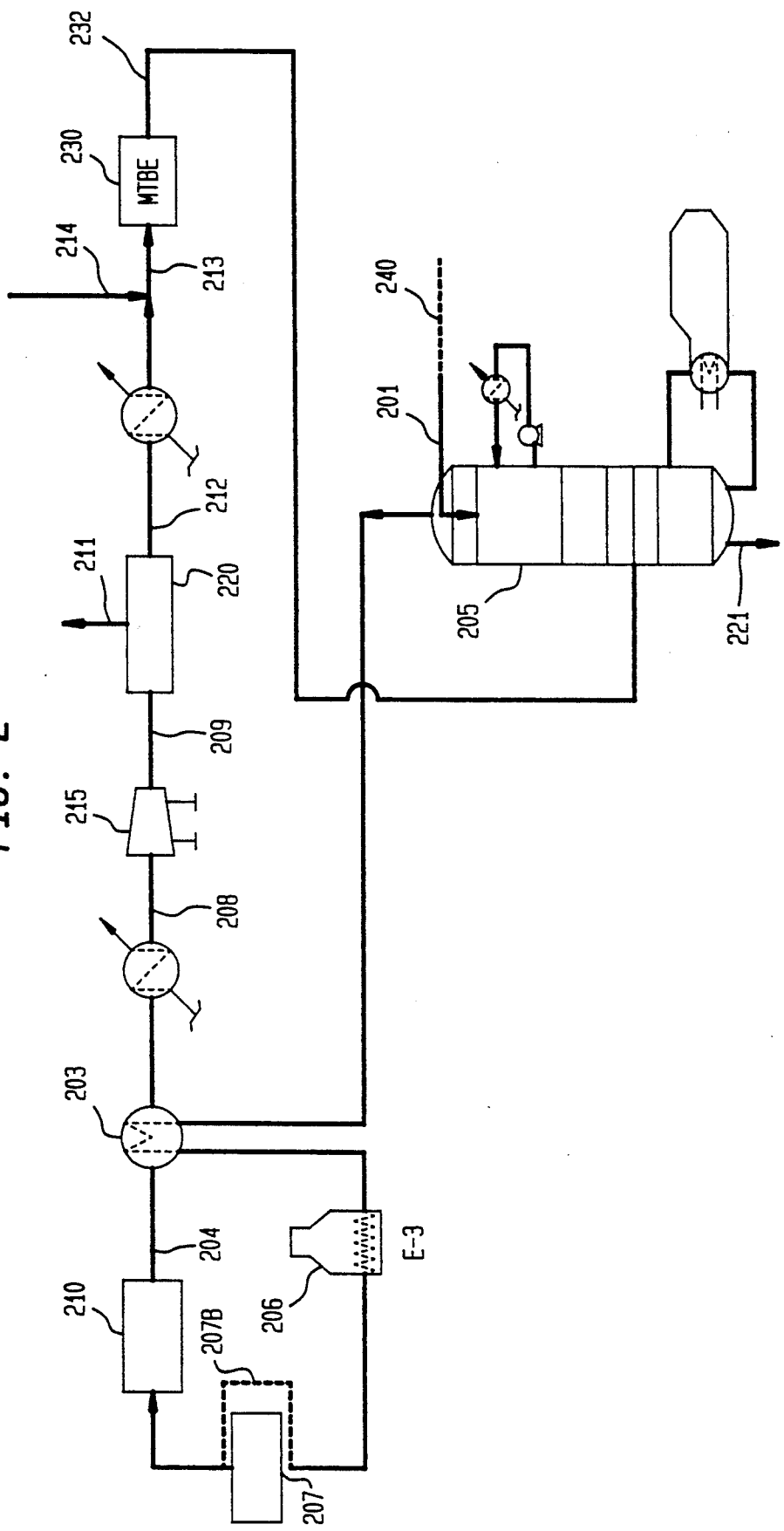
FIG. 2 is a schematic diagram of a preferred embodiment of the invention that also illustrates recycle of the vapor comprising unconverted components from the etherification effluent.

A particularly preferred embodiment of the invention is presented in process flow diagram FIG. 2 illustrating the conversion of isobutane to MTBE wherein isobutane-rich $C_4$ feedstream is introduced initially utilized as reflux to the debutanizer. Using the hydrocarbon feedstock as reflux offers the following improvements and advantages to the novel process of the invention: provides sufficient hydrocarbon volume to separate unconverted alkanol into the overhead stream; provides an efficient method to vaporize the feed; eliminates the overhead condenser system; and cools the tower rectifying sections to minimize tower overhead pressure requirements which, in turn, minimizes the process compressor requirements. The tower overhead is utilized in the depicted process as recycle feedstream to the dehydrogenation zone.

The major units of the process as illustrated in FIG. 2 include the debutanizer 205 (or depentanizer if a $C_5+$ feed is employed), the dehydrogenation reactor 210, compressor 215, membrane separation unit 220, and the vapor phase etherification reactor 230. An isobutane feedstream 201 at a pressure of about 90 psi (630 kPa) and temperature of 95° F. (35° C.) is introduced into a top portion of debutanizer 205 as reflux to separate the effluent 232 from the etherification reactor 230. Optionally, as shown by dash lines, line 201 may contain an expansion valve 240 whereby the inlet temperature of the feedstream to the tower is lowered. The debutanizer overhead stream temperature is increased to approximately 1,080° F. (582° C.) at a pressure of 75 psi (525 kPa) by heat exchange 203 with dehydrogenation reaction zone effluent 204 and by heating with preheater 206.

Optionally, the etherification effluent stream containing unreacted olefin and/or alkanol may be preconverted in MOG reactor unit 207 before passing to the dehydrogenation zone 210. In addition to the isobutane feedstock, includes unreacted methanol, olefins, and isobutane unconverted in the dehydrogenation step. Dehydrogenation of the effluent from reactor 207 or optional bypass 207B around unit 207 is carried out under conventional dehydrogenation conditions known in the art to produce the dehydrogenation effluent 204 at a pressure of approximately 55 psi (385 kPa) and 1,030° F. (554° C.). The effluent comprises an isobutene rich feed. Following heat exchange, the effluent vapor is passed 208 to compressor 215 where it is pressurized to a pressure of approximately 125 psi (875 kPa) at a temperature of 191° F. (88° C.) and introduced 209 to membrane separator 220. In the membrane separation section, hydrogen and light hydrocarbon purge gas stream 211 are separated and an effluent stream 212 comprising isobutene at a pressure of 115 psi (805 kPa) and temperature of 191° F. (88° C.) is produced. Following heat exchange, the effluent stream 212 is introduced 213 into MTBE etherification zone 230 in conjunction with methanol feedstream 214 at a pressure of 110 psi (770 kPa) and a temperature of 140° F. (60° C.). Etherification is carried out in etherification zone 230 in contact with acidic etherification catalyst under vapor phase etherification conditions. The etherification effluent stream 232, which is recovered at a pressure of about 105 psi (735 kPa) and temperature of about 143° F. (62° C.)' is passed to debutanizer 205 at a pressure of about 93 psi (651 kPa) and 126 (41° C.) and 140° F. (60° C.) respectively, following heat exchange 218 and separator 219. The MTBE product is recovered from the debutanizer as a bottom stream 221 at a temperature of about 255° F. (124° C.) and pressure of about 97 psi (679 kPa). While in the foregoing description of the process of the invention the membrane separation step is carried out upstream of the etherification step, it is with the purview of the invention to carry out the membrane separation step downstream of the etherification step.

The feedstream and product quantities for the isobutane dehydrogenation and MTBE production process depicted in FIG. 2 is summarized in Table 1 in mass basis units of pounds per hour. As shown in Table 1, an isobutane feedstream of 101,508 pounds per hour produces a total of 133,155 pounds per hour of methyl tertiary butyl ether. The combined feed to the dehydrogenation reactor consisting of recycle plus isobutane feed is about 263,294 pounds per hour.

TABLE 1

| ISOBUTANE DEHYDROGENATION/MTBE PROCESS Mass Basis, lbs/hr: | | | |
| --- | --- | --- | --- |
| COMPONENTS | ISOBUTANE FEED | MEOH FEED | MTBE PRODUCT |
| ISOBUTANE | 101508 | | 2498 |
| 1-BUTENE | | | 48 |
| N-BUTANE | | | 204 |
| ISOBUTENE | | | 90 |
| METHANOL | | 47369 | |
| MTBE | | | 130315 |
| H$_2$O | | 790 | |
| TOTAL | 101508 | 48159 | 133155 |

*COMBINED FEED (RECYCLE + ISOBUTANE FEED) TO DEHYDROGENATION UNIT = 263,294 LBS/HR

While the invention has been described by reference to specific embodiments, there is no intent to limit the scope of the invention except as described in the following claims.

We claim:

1. A process for the production of alkyl tertiary alkyl ethers, comprising:

contacting a hydrocarbon feedstream rich in iso-olefins in the vapor phase and a $C_1$–$C_3$ alkanol feedstream with acidic shape selective zeolite etherification catalyst particles in an etherification zone under etherification conditions whereby an effluent stream is produced comprising said alkyl tertiary alkyl ethers, unreacted $C_1$–$C_3$ alkanol and hydrocarbons;

passing said effluent stream to a fractionator and separating said etherification effluent stream in contact with a reflux stream comprising fresh hydrocarbon feedstock rich in isoparaffins whereby a bottom stream is recovered comprising said ethers and an overhead stream is separated comprising said unreacted alkanol and hydrocarbons rich in isoparaffins;

converting at least a portion of said overhead stream in a dehydrogenation zone in contact with dehydrogenation catalyst under vapor phase dehydrogenation conditions whereby a dehydrogenation effluent vapor stream is produce rich in iso-olefins and hydrogen;

compressing said dehydrogenation effluent and separating said hydrogen therefrom with a selective membrane to recover hydrogen byproduct and a retentate stream rich in iso-olefin;

recycling said retentate stream to said etherification zone in vapor phase.

2. The process of claim 1 wherein said etherification zone effluent stream is separated in a debutanizer to produce a bottom stream comprising said alkyl tertiary alkyl ether and an overhead stream comprising said unreacted alkanol, unreacted iso-olefins and isoparaffins.

3. The process of claim 1 wherein said isoparaffin comprises isobutane, said iso-olefin comprises isobutene, said alkanol comprises methanol; whereby methyl tertiary butyl ether is produced.

4. The process of claim 1 wherein said isoparaffin comprises isopentane, said iso-olefin comprises isoamylene, said alkanol comprises methanol; whereby methyl tertiary amyl ether is produced.

5. The process of claim 1 wherein said etherification conditions comprise mixed vapor/liquid phase comprising at least 50 wt % vapor.

* * * * *